(12) United States Patent
Zajac

(10) Patent No.: US 8,759,542 B2
(45) Date of Patent: Jun. 24, 2014

(54) PROCESS FOR PREPARING ALPHA-CARBOXAMIDE DERIVATIVES

(75) Inventor: Matthew Allen Zajac, King of Prussia, PA (US)

(73) Assignee: Convergence Pharmaceuticals Limited, London (GB)

( * ) Notice: Subject to any disclaimer, the term of this patent is extended or adjusted under 35 U.S.C. 154(b) by 42 days.

(21) Appl. No.: 13/393,174

(22) PCT Filed: Sep. 1, 2010

(86) PCT No.: PCT/EP2010/062826
§ 371 (c)(1),
(2), (4) Date: May 21, 2012

(87) PCT Pub. No.: WO2011/029762
PCT Pub. Date: Mar. 17, 2011

(65) Prior Publication Data
US 2012/0226053 A1 Sep. 6, 2012

Related U.S. Application Data

(60) Provisional application No. 61/242,003, filed on Sep. 14, 2009.

(51) Int. Cl.
C07D 207/09 (2006.01)
(52) U.S. Cl.
CPC .................................. *C07D 207/09* (2013.01)
USPC ........................................................ 548/537
(58) Field of Classification Search
CPC .................................................. C07D 207/09
USPC ........................................................ 548/537
See application file for complete search history.

(56) References Cited

FOREIGN PATENT DOCUMENTS

| WO | WO 2005/110982 A2 | 11/2005 |
| WO | WO 2007/042239 A1 | 4/2007 |
| WO | WO 2007/042240 A1 | 4/2007 |
| WO | WO 2007/042250 A1 | 4/2007 |
| WO | WO 2008/090116 A1 | 7/2008 |
| WO | WO 2008/122546 A1 | 10/2008 |

OTHER PUBLICATIONS

McManus et al. (Chem. Rev. 2004, 104, 4151-420).*
Mancheno et al. (J. Am. Chem. Soc., 2004, 126, 456-457).*
International Search Report for PCT/EP2010/062826, dated Dec. 16, 2010.
Lygo et al., "Co-catalyst enhancement of enantioselective PTC Michael additions involving glycine imines", Tetrahedron Letters, vol. 50, No. 26, Jul. 1, 2009, pp. 3363-3365, XP026120504.
Kanemasa et al., "Stereoselective Michael Addition of the Imines of alpha-Amino Esters in the Presence of Lithium Bromide/1,8-Diazabicyclo-[5.4.0]undec-7-ene", Journal of Organic Chemistry, vol. 55, No. 14, 1990, pp. 4411-4417, XP002607994.

* cited by examiner

*Primary Examiner* — Robert Havlin
(74) *Attorney, Agent, or Firm* — Foley & Lardner LLP

(57) ABSTRACT

The present application provides a process for the preparation of α-carboxamide pyrrolidine derivatives of formula (I), wherein $R^1$ and $R^2$ are independently hydrogen, $C_{1-6}$alkyl or $C_{3-6}$cycloalkyl$C_{1-6}$alkyl; or such $R^1$ and $R^2$, together with the nitrogen to which they are attached, may form an unsubstituted 3-, 4-, 5- or 6-membered saturated ring; X is carbon or nitrogen; n is 0, 1 or 2, wherein when present each $R^5$ is independently selected from the list consisting of $C_{1-3}$alkyl, halogen, cyano, halo$C_{1-3}$alkyl, hydroxy, $C_{1-3}$alkoxy and $C_{1-3}$haloalkoxy; either $R^6$ or $R^7$ is —O—$R^8$, —OCHR$^9$R$^8$, —NCH$_2$R$^8$ or —(CH$_2$)$_2$R$^8$ wherein the other $R^6$ or $R^7$ is hydrogen or $R^5$; and wherein $R^8$ is a phenyl ring or wherein the phenyl ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy; and $R^9$ is hydrogen or $C_{1-3}$alkyl.

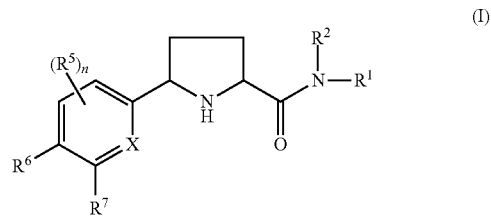

(I)

2 Claims, No Drawings

PROCESS FOR PREPARING ALPHA-CARBOXAMIDE DERIVATIVES

The present invention relates to a process for preparing some α-carboxamide pyrrolidine derivatives. Particularly, the invention relates to a new and useful process for preparing α-carboxamide pyrrolidine derivatives, starting from an alkyl N-(diphenylmethylidene)glycinate derivative and 1-(hetero)aryl-2propen-1 ones.

The general process disclosed in the art for the preparation of such α-carboxamide pyrrolidine derivatives (which are useful as modulators of use-dependent voltage gated sodium channels) is reported in PCT application WO2007/042250.

However, there is a need for the development of alternative processes for the preparation of such α-carboxamide pyrrolidine derivatives, which are capable of practical application to large scale manufacture.

The present invention provides a particularly advantageous process of preparing α-carboxamide pyrrolidine derivatives.

Thus, the present invention provides a process for the preparation of α-carboxamide pyrrolidine derivatives of formula (I),

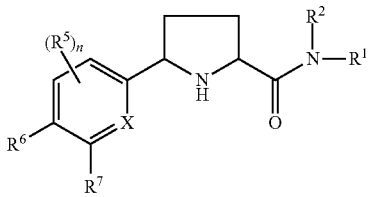
(I)

wherein $R^1$ and $R^2$ are independently hydrogen, $C_{1-6}$alkyl or $C_{3-6}$cycloalkyl$C_{1-6}$alkyl; or such $R^1$ and $R^2$, together with the nitrogen to which they are attached, may form an unsubstituted 3-, 4-, 5- or 6-membered saturated ring;

X is carbon or nitrogen;

n is 0, 1 or 2, wherein when present each $R^5$ is independently selected from the list consisting of $C_{1-3}$alkyl, halogen, cyano, halo$C_{1-3}$alkyl, hydroxy, $C_{1-3}$alkoxy and $C_{1-3}$haloalkoxy;

either $R^6$ or $R^7$ is —O—$R^8$, —OCHR$^9$R$^8$, —NCH$_2$R$^8$ or —(CH$_2$)$_2$R$^8$ wherein the other $R^6$ or $R^7$ is hydrogen or $R^5$; and wherein $R^8$ is a phenyl ring or wherein the phenyl ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy; and $R^9$ is hydrogen or $C_{1-3}$alkyl;

which comprises:

(a) reacting a compound of formula (II)

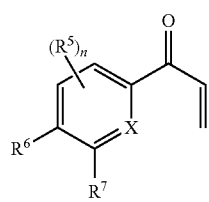
(II)

wherein X, $R^5$, $R^6$, $R^7$ and n are as above defined, with a compound of formula (III)

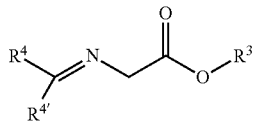
(III)

wherein $R^3$ is C1-4 alkyl and $R^4$ and $R^{4'}$ may be each an optionally substituted phenyl ring in the presence of an organic aprotic solvent, an amine base, a chiral ligand and an appropriate Cu(I) salt, under conditions of time and temperature sufficient to produce the corresponding compound of formula (IV)

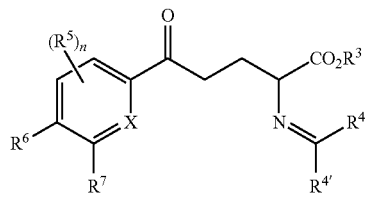
(IV)

wherein X, $R^5$, $R^6$, $R^7$, $R^3$, $R^4$, $R^{4'}$ and n are as above defined; and wherein the chiral ligand is selected in the group consisting of:

(R)-1-[(S)-2-(Diphenylphosphino)ferrocenyl]ethyldicyclohexylphosphine ethanol adduct;
(S)-1-[(R)-2-(Diphenylphosphino)ferrocenyl]ethyldicyclohexylphosphine ethanol adduct;
(R)-1-[(S)-2-Diphenylphosphinoferrocenyfl]ethyldi-tert.-butylphosphine;
(S)-1-[(R)-2-Diphenylphosphinoferrocenyl]ethyldi-tert.-butylphosphine;
(R)-1-[(S)-2-Dicyclohexylphosphino)ferrocenyl]ethyldicyclohexylphosphine;
(S)-1-[(R)-2-Dicyclohexylphosphino)ferrocenyl]ethyldicyclohexylphosphine;
(R)-1-[(S)-2-Diphenylphosphino)-ferrocenyl]ethyl-di-3,5-xylylphosphine;
(S)-1-[(R)-2-Diphenylphosphino)-ferrocenyl]ethyl-di-3,5-xylylphosphine; (R)-1-[(S)-2-Di-(3,5-bis(trifluoromethyl)phenyl)phosphino)-ferrocenyl]ethyldicyclohexylphosphine;
(S)-1-[(R)-2-Di-(3,5-bis(trifluoromethyl)phenyl)phosphino)-ferrocenyl]ethyldicyclohexylphosphine;
(R)-1-[(S)-2-Di-(4-methoxy-3,5-dimethylphenyl)phosphino)-ferrocenyl]ethyldicyclohexylphosphine;
(S)-1-[(R)-2-Di-(4-methoxy-3,5-dimethylphenyl)phosphino)-ferrocenyl]ethyldicyclohexylphosphine;
(R)-1-[(S)-2-Di-(3,5-bis(trifluoromethyl)phenyl)phosphino)-ferrocenyl]ethyldi-(3,5-xylyl)phosphine;
(S)-1-[(R)-2-Di-(3,5-bis(trifluoromethyl)phenyl)phosphino)-ferrocenyl]ethyldi-(3,5-xylyl)phosphine;
(R)-1-[(S)-2-Dicyclohexylphosphino)ferrocenyl]-ethyldi-tert.-butylphosphine;
(S)-1-[(R)-2-Dicyclohexylphosphino)ferrocenyl]-ethyldi-tert.-butylphosphine;
(R)-1-[(S)-2-Di-(4-trifluoromethylphenyl)phosphino)ferrocenyl]ethyldi-tert.-butylphosphine;
(S)-1-[(R)-2-Di-(4-trifluoromethylphenyl)phosphino)ferrocenyl]ethyldi-tert.-butylphosphine;
(R)-1-[(S)-2-(Di-2-furylphosphino)-ferrocenyl]ethyldi-3,5-xylylphosphine;

(S)-1-[(R)-2-(Di-2-furylphosphino)-ferrocenyl]ethyldi-3,5-xylylphosphine;
(R)-4-Isopropyl-2-[(R)-2-(diphenylphosphino)ferrocen-1-yl]oxazoline;
(S)-4-Isopropyl-2-[(S)-2-(diphenylphosphino)ferrocen-1-yl]oxazoline;
(S)-1-Diphenylphosphino-2-[(R)-α-(N,N-dimethylamino)-o-diphenylphosphinophenyl)methyl]ferrocene;
(R)-1-Diphenylphosphino-2-[(S)-α-(N,N-dimethylamino)-o-diphenylphosphinophenyl)methyl]ferrocene;
(R)-1-[(R)-2-(2'-Diphenylphosphinophenyl)ferrocenyl]ethyldi(bis-3,5-trifluoromethylphenyl)phosphine;
(S)-1-[(S)-2-(2'-Diphenylphosphinophenyl)ferrocenyl]ethyldi(bis-3,5-trifluoromethylphenyl)phosphine;
(R)-1-[(R)-2-(2'-Diphenylphosphinophenyl)ferrocenyl]-ethyldiphenylphosphine;
(S)-1-[(S)-2-(2'-Diphenylphosphinophenyl)ferrocenyl]-ethyldiphenylphosphine;
(S)-1-[(S)-2-{2'-Di(3,5-dimethyl-4-methoxyphenyl)phosphinophenyl}-ferrocenyl]ethyldi(bis-3,5-trifluoromethylphenyl)phosphine;
(R)-1-[(R)-2-{2'-Di(3,5-dimethyl-4-methoxyphenyl)phosphinophenyl}-ferrocenyl]ethyldi(bis-3,5-trifluoromethylphenyl)phosphine;
(αR,αR)-2,2'-Bis(α-N,N-dimethylaminophenylmethyl)-(S,S)-1,1'bis(diphenylphosphino)ferrocene;
(αS,αS)-2,2'-Bis(α-N,N-dimethylaminophenylmethyl)-(R,R)-1,1bis(diphenylphosphino)ferrocene;
(αR,αR)-2,2'-Bis(α-N,N-dimethylaminophenylmethyl)-(S,S)-1,1'-bis(dicyclohexylphosphino)-ferrocene;
(αS,αS)-2,2'-Bis(α-N,N-dimethylaminophenylmethyl)-(R,R)-1,1'-bis(dicyclohexylphosphino)-ferrocene;
(αR,αR)-2,2'-Bis(α-N,N-dimethylaminophenylmethyl)-(S,S)-1,1'-bis-[di(bis-(3,5-trifluoromethyl)phenyl)-phosphino]ferrocene;
(αS,αS)-2,2'-Bis(α-N,N-dimethylaminophenylmethyl)-(R,R)-1,1'-bis[di(bis-(3,5-trifluoromethyl)phenyl)-phosphino]ferrocene;
(αR,αR)-2,2'-Bis(α-N,N-dimethylaminophenylmethyl)-(S,S)-1,1'-bis[di(3,5-dimethyl-4-methoxyphenyl)phosphino]ferrocene;
(αS,αS)-2,2'-Bis(α-N,N-dimethylaminophenylmethyl)-(R,R)-1,1'-bis[di(3,5-dimethyl-4-methoxyphenyl)phosphino]ferrocene;
Hydroquinidine(anthraquinone-1,4-diyl)diether;
Hydroquinidine-2,5-diphenyl-4,6-pyrimidinediyl diether;
(S)-(−)-2,2'-Bis(di-p-tolylphosphino)-1,1'-binaphthyl
And (R)-(+)-2,2'-Bis(di-p-tolylphosphino)-1,1'-binaphthyl (b) reacting a compound of formula (IV) in aqueous acidic media under conditions of time and temperature sufficient to produce the compound of formula (V) after neutralization with an appropriate base

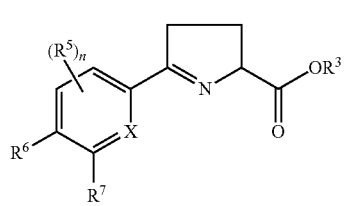

(V)

wherein X, $R^5$, $R^6$, $R^7$, $R^3$, $R^4$, $R^{4'}$ and n are as above defined;

(c) reacting a compound of formula (V) with Pt/C under an atmosphere of hydrogen at elevated pressure (such as 2 atm) in a suitable protic solvent at room temperature for a time sufficient to give a compound of formula (VI)

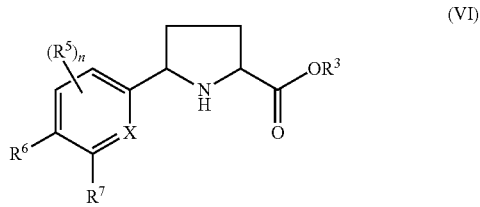

(VI)

wherein X, $R^5$, $R^6$, $R^7$, $R^3$, $R^4$, $R^{4'}$ and n are as above defined; and (d) reacting a compound of formula (VI) with a solution of an appropriate amine NR1R2 (for example a concentrated solution, such as 7N or 11.2 M solution) in an appropriate protic solvent (such as methanol) and at the appropriate temperature (for example room temperature) for a period of time sufficient to produce compounds of formula (I).

Compounds of formula (I) may be converted into their corresponding pharmaceutically acceptable salts according to procedures available in the art and well known to the skilled person.

In one embodiment, the compound of formula (IV) produced in step (a) of the above described process may be conveniently used directly in the subsequent step (b) without being isolated.

In one aspect of the present invention a compound of formula (IV) is provided as intermediate of the above described process

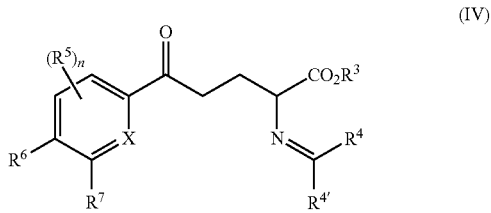

(IV)

wherein X, $R^5$, $R^6$, $R^7$, $R^3$, $R^4$, $R^{4'}$ and n are as above defined.

In one embodiment, the compound of formula (VI) produced in step (c) of the above described process may be conveniently used directly in the subsequent step (d) without being isolated.

In a further embodiment, the compound of formula (IV) produced in step (a) of the above described process may be conveniently used directly in the subsequent step (b) without being isolated and the compound of formula (VI) produced in step (c) of the above described process may be conveniently used directly in the subsequent step (d) without being isolated.

It will be appreciated by the person skilled in the art that at least four possible stereoisomers may exist for compounds of formula (I), i.e. compounds of formula (Ia), (Ib), (Ic) and (Id). These are shown below:

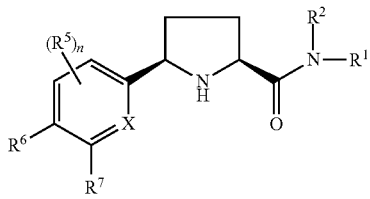
(Ia)

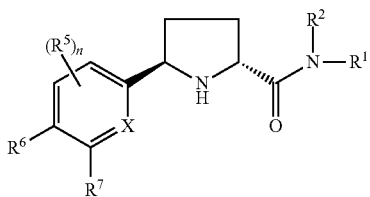
(Ib)

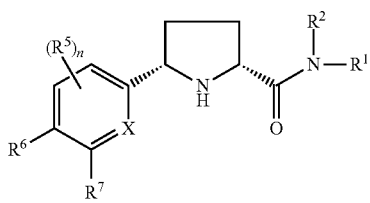
(Ic)

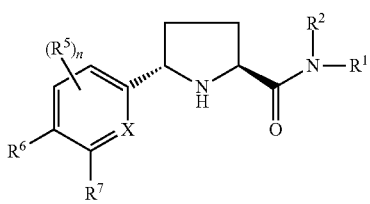
(Id)

The present invention provides a process to prepare compounds of formula (Ia), (Ib), (Ic) or (Id)

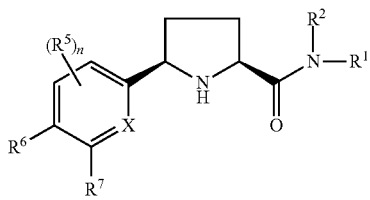
(Ia)

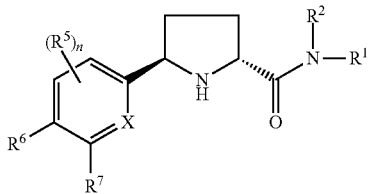
(Ib)

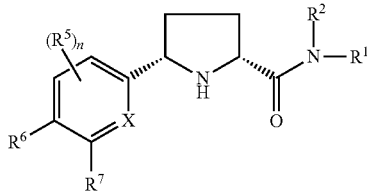
(Ic)

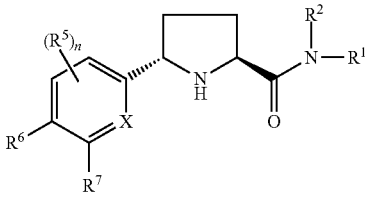
(Id)

wherein $R^1$, $R^2$, $R^5$, $R^6$, $R^7$, X, n and q are as defined above.

In one embodiment, the present invention provides a process to prepare compounds of formula (Ia) or (Ic)

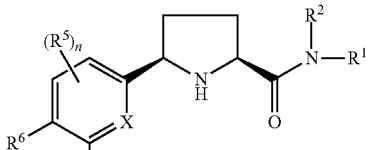
(Ia)

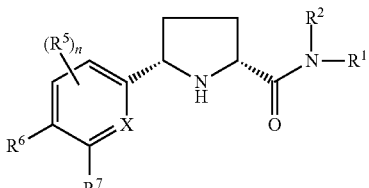
(Ic)

wherein $R^1$, $R^2$, $R^5$, $R^6$, $R^7$, X, n and q are as defined above.

In another embodiment, the present invention provides a process to prepare compounds of formula (Ia)

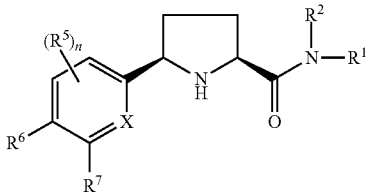
(Ia)

wherein $R^1$, $R^2$, $R^5$, $R^6$, $R^7$, X, n and q are as defined above.

Unless otherwise indicated, any alkyl group is straight or branched regardless of whether it forms part of another group, for example, alkoxy, haloalkyl and haloalkoxy.

As used herein, a haloalkyl group means an alkyl group substituted by one or more halogen atoms. A haloalkoxy group should be similarly construed.

The term 5- or 6-membered aromatic heterocyclic ring means a heterocyclyl group containing one or more carbon atoms, one or more hydrogen atoms and one or more heteroatoms such as nitrogen, oxygen and sulfur; the carbon and heteroatoms being interconnected to form a ring. For example furyl, thienyl, pyrrolyl, imidazolyl, oxazolyl, thiazolyl, pyrazolyl, isoxazolyl, isothiazolyl, oxadiazolyl, triazolyl, thiadiazolyl, pyridyl, pyridazinyl, pyrimidinyl, pyrazinyl and tetrazolyl.

Halo means fluoro, chloro, bromo or iodo.

In an embodiment, X is carbon.

In another embodiment, X is nitrogen.

In an embodiment, n is 0 or 1. In another embodiment n is 0.

In an embodiment, $R^1$ and $R^2$ are independently H or $C_{1-6}$alkyl. In an alternative embodiment, $R^1$ and $R^2$ are both H.

In an embodiment, $R^6$ is —$OCH_2R^8$, and $R^7$ is hydrogen or $R^5$; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$ alkyl, hydroxy, $C_{1-3}$alkoxy and $C_{1-3}$haloalkoxy.

In an embodiment, $R^9$ is hydrogen or methyl. In another embodiment, $R^9$ is hydrogen.

In one embodiment the compound of formula (I) is (5R)-5-(4-{[(2-fluorophenyl)methyl]oxy}phenyl)-L-prolinamide.

Examples of aprotic solvents which may be used in the reaction include THF, dimethoxyethane, tert-butyl methyl ether, diethyl ether, diisopropyl ether, cyclohexane, toluene, benzene, ethyl acetate, dichloromethane, triethyl amine and the like and any mixtures thereof.

Examples of amine bases which may be used in the reaction include pyridine, imidazole, 2,6 lutidine, piperidine, dibutylamine, diisopropylamine, phenyl ethylamine, ethyl butylamine, ethyl butylamine, tetramethyl guanidine (TMG), cyclohexyl-tetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0]undec-7-ene (DBU), triethylamine and the like, and mixtures of any two or more thereof, Examples of Cu(I) salts which may be used in the reaction include $Cu(MeCN)_4PF_6$, $Cu(MeCN)_4ClO_4$ and complexes of the form, CuX where X=F, Cl, Br, I, —$OSO_2$Aryl and alternate solvated versions thereof.

Examples of protic solvents which may be used in the reaction include water, methanol, ethanol, isopropanol, tert-butanol, tert-amyl alcohol and the like, and mixtures of any two or more thereof.

Examples of acidic media which can be used for removal of the diphenyl group include aqueous mixtures of HF, HCl, HBr, HI, H2SO4, trifluoroacetic acid, sulfonic acids, and the like, and buffered versions thereof.

Examples of bases which can be used for neutralization include bases of alkali metals and alkaline earth metals such as sodium hydroxy, potassium hydroxy, lithium hydroxy and the like, alkali metal carbonates and bicarbonates such as sodium carbonate, potassium bicarbonate and the like, pyridine, imidazole, 2,6 lutidine, piperidine, dibutylamine, diisopropylamine, phenyl ethylamine, ethyl butylamine, ethyl butylamine, tetramethyl guanidine (TMG), cyclohexyl-tetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0]undec-7-ene (DBU), triethylamine and the like, and mixtures of any two or more thereof, In one embodiment, for step (a), the organic solvent is tetrahydrofuran (THF).

In one embodiment, for step (a), the base is DBU.

In one embodiment, for step (a), the ligand is (S)-4-Isopropyl-2-[(S)-2-(diphenylphosphino)ferrocen-1-yl]oxazoline.

In one embodiment, for step (a), the Cu(I) complex is $Cu(MeCN)_4PF_6$.

In one embodiment, for step (b) the acidic media is aqueous 1M $H_2SO_4$ dissolved in THF.

In one embodiment, for step (c), the catalyst is 5% Pt/C.

In one embodiment, for step (d) the compound of formula (VI) is reacted with a solution of ammonia in methanol.

In one embodiment, for step (a) the ligand is (S)-4-Isopropyl-2-[(S)-2-(diphenylphosphino)ferrocen-1-yl]oxazoline and the Cu(I) complex is $Cu(MeCN)_4PF_6$.

In another embodiment, the compound of formula (I) obtained is (5R)-5-(4-{[(2-fluorophenyl)methyl]oxy}phenyl)-L-prolinamide and for step (a) the compound of formula (II) is 1-(4-[2-fluorobenzyloxy]phenyl)-2-propen-1-one, the ligand is (S)-4-Isopropyl-2-[(S)-2-(diphenylphosphino)ferrocen-1-yl]oxazoline and Cu(I) complex is $Cu(MeCN)_4PF_6$.

In one embodiment, for step (a) the base is DBU, the ligand is (S)-4-Isopropyl-2-[(S)-2-(diphenylphosphino)ferrocen-1-yl]oxazoline and Cu(I) complex is $Cu(MeCN)_4PF_6$.

In another embodiment, the compound of formula (I) obtained is (5R)-5-(4-{[(2-fluorophenyl)methyl]oxy}phenyl)-L-prolinamide and for step (a) the compound of formula (II) is 1-(4-[2-fluorobenzyloxy]phenyl)-2-propen-1-one, the base is DBU, the ligand is (S)-4-Isopropyl-2-[(S)-2-(diphenylphosphino)ferrocen-1-yl]oxazoline and Cu(I) complex is $Cu(MeCN)_4PF_6$.

In one embodiment, for step (a) the organic solvent is tetrahydrofuran (THF), the base is DBU, the ligand is (S)-4-Isopropyl-2-[(S)-2-(diphenylphosphino)ferrocen-1-yl]oxazoline and Cu(I) complex is $Cu(MeCN)_4PF_6$.

In another embodiment, the compound of formula (I) obtained is (5R)-5-(4-{[(2-fluorophenyl)methyl]oxy}phenyl)-L-prolinamide and for step (a) the compound of formula (II) is 1-(4-[2-fluorobenzyloxy]phenyl)-2-propen-1-one, the organic solvent is tetrahydrofuran (THF), the base is DBU, the ligand is (S)-4-Isopropyl-2-[(S)-2-(diphenylphosphino)ferrocen-1-yl]oxazoline and Cu(I) complex is $Cu(MeCN)_4PF_6$.

In one embodiment, for step (a) the organic solvent is tetrahydrofuran (THF), the base is DBU, the ligand is (S)-4-Isopropyl-2-[(S)-2-(diphenylphosphino)ferrocen-1-yl]oxazoline and Cu(I) complex is $Cu(MeCN)_4PF_6$ and for step (b) the acidic media is aqueous 1M $H_2SO_4$ dissolved in THF.

In another embodiment, the compound of formula (I) obtained is (5R)-5-(4-{[(2-fluorophenyl)methyl]oxy}phenyl)-L-prolinamide, for step (a) the compound of formula (II) is 1-(4-[2-fluorobenzyloxy]phenyl)-2-propen-1-one, the organic solvent is tetrahydrofuran (THF), the base is DBU, the ligand is (S)-4-Isopropyl-2-[(S)-2-(diphenylphosphino)ferrocen-1-yl]oxazoline and Cu(I) complex is $Cu(MeCN)_4PF_6$ and for step (b) the acidic media is aqueous 1M $H_2SO_4$ dissolved in THF.

In one embodiment, for step (a) the organic solvent is tetrahydrofuran (THF), the base is DBU, the ligand is (S)-4-Isopropyl-2-[(S)-2-(diphenylphosphino)ferrocen-1-yl]oxazoline and Cu(I) complex is $Cu(MeCN)_4PF_6$, for step (b) the acidic media is aqueous 1M $H_2SO_4$ dissolved in THF and for step (c) the catalyst is 5% Pt/C.

In another embodiment, the compound of formula (I) obtained is (5R)-5-(4-{[(2-fluorophenyl)methyl]oxy}phenyl)-L-prolinamide, for step (a) the compound of formula (II) is 1-(4-[2-fluorobenzyloxy]phenyl)-2-propen-1-one, the organic solvent is tetrahydrofuran (THF), the base is DBU, the ligand is (S)-4-Isopropyl-2-[(S)-2-(diphenylphosphino)ferrocen-1-yl]oxazoline and Cu(I) complex is Cu(MeCN)$_4$PF$_6$, for step (b) the acidic media is aqueous 1M H$_2$SO$_4$ dissolved in THF and for step (c) the catalyst is 5% Pt/C.

In a further embodiment, the compound of formula (I) obtained is (5R)-5-(4-{[(2-fluorophenyl)methyl]oxy}phenyl)-L-prolinamide, for step (a) the compound of formula (II) is 1-(4-[2-fluorobenzyloxy]phenyl)-2-propen-1-one, the organic solvent is tetrahydrofuran (THF), the base is DBU, the ligand is (S)-4-Isopropyl-2-[(S)-2-(diphenylphosphino)ferrocen-1-yl]oxazoline and Cu(I) complex is Cu(MeCN)$_4$PF$_6$, for step (b) the acidic media is aqueous 1M H$_2$SO$_4$ dissolved in THF, for step (c) the catalyst is 5% Pt/C and for step (d) the compound of formula (VI) is reacted with a solution of ammonia in methanol.

The amount of solvent utilized in the process of the invention is preferably at least the amount necessary to solubilize the carbamate salt present.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

EXPERIMENTAL

The following example is intended for illustration only and is not intended to limit the scope of the invention in any way, the invention being defined by the claims which follow.

In the procedures that follow, after each starting material, reference to a Preparation or Example by number is typically provided. This is provided merely for assistance to the skilled chemist. The starting material may not necessarily have been prepared from the batch referred to.

In the Example, Nuclear Magnetic Resonance (NMR) spectra were recorded on a Bruker instrument at 400 MHz for proton and 100 MHz for carbon. Chemical shifts are reported in ppm (δ) using the residual solvent line as internal standard. Splitting patterns are designed as s, singlet; d, double; t, triple; q, quartet; m, multiplet; b, broad. The NMR spectra were recorded at temperatures ranging from 15 to 25° C. High Performance Liquid Chromatography (HPLC) spectra were acquired with Agilent Technology HP 1200 LC system equipped with an Agilent Zorbax SB-C18 (50×3 mm, 1.8μ) Rapid Resolution HT as column; DAD UV chromatographic traces are typically taken on PDA detector; the method used a gradient 0-100% B in 3 minutes, with Mobile phase A: Water+0.05% TFA; Mobile Phase B: acetonitrile+0.05% TFA and a flow of 1.0 ml/min and a temperature of 60° C.; A=220 nm. Liquid Chromatography Mass Spectroscopy (LC-MS) gave low resolution mass Spectroscopy (LRMS) data and were obtained by using Agilent LC/MSD 1100 Series Mass Spectrometer, operating in ES (+) and ES (−) electrospray ionization mode coupled with HPLC instrument Agilent 1100 Series (described above).

Abbreviations:
THF=tetrahydrofuran
DMSO=dimethylsulfoxide
TBME=tert-butyl methyl ether
BHT=Butylated hydroxytoluene
PTFE=Polytetrafluoroethylene
DBU=diaza(1,3)bicycle[5.4.0]undecane Preparation 1: Methyl 4-(2-fluorobenzyloxy)benzoate (P1)

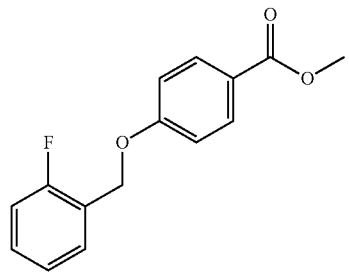 [SMILES: COC(=O)c1ccc(OCc2ccccc2F)cc1]

Methylparaben (8.85 g, 58.19 mmol) and K$_2$CO$_3$ (16.1 g, 116.38 mmol) were stirred in acetonitrile (100 mL) for 5 minutes and then 2-fluorobenzyl bromide (10 g, 52.9 mmol) was added. The suspension was heated to 50-55° C. and held for 2 hours. The mixture was then cooled to 20-25° C., filtered, and the filtrate solution concentrated to a thick residue. The residue was then dissolved in CH$_2$Cl$_2$, washed with a 1 M Na$_2$CO$_3$ solution, dried over Na$_2$SO$_4$, and concentrated to a solid. The solid was then stirred vigorously for 1 hour in just enough hexanes to allow for agitation (~40 mL) and then cooled to 0-5° C. After 15 minutes, the product was isolated by filtration and washed with ~25 mL of hexanes. After drying under vacuum, 1 was isolated as a white solid (13.1 g, 87% yield).

$^1$H NMR (400 MHz, DMSO-d$_6$) δ 7.96-7.90 (2H, m), 7.57 (2H, apparent td, J=7.7, 1.8 Hz), 7.48-7.39 (1H, m), 7.30-7.21 (2H, m), 7.17-7.12 (2H, m), 5.22 (2H, s), 3.81 (3H, s).

$^{13}$C NMR (100 MHz, DMSO-d$_6$) δ 166.2, 162.4, 160.8 (d, J=247 Hz), 131.6, 131.1 (d, J=3.8 Hz), 131.0 (d, J=8.3 Hz), 124.9 (d, J=3.4 Hz), 123.5 (d, J=14.1 Hz), 122.6, 115.8 (d, J=21.0 Hz), 115.0, 64.2 (d, J=3.4 Hz), 52.2.

LRMS (m/e): 261.3 [MH]$^+$.

Preparation 2: 4-(2-fluorobenzyloxy)benzoic acid (P2)

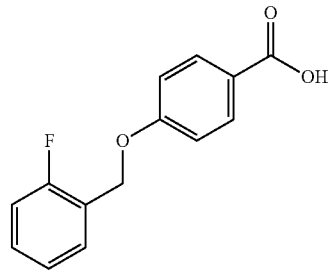 [SMILES: O=C(O)c1ccc(OCc2ccccc2F)cc1]

Methyl 4-(2-fluorobenzyloxy)benzoate (P1, 10.0 g, 26.9 mmol) was dissolved in methanol (60 mL) and THF (90 mL). A 45 wt % potassium hydroxide solution (20 mL) was then added and the resulting exotherm was controlled by a water bath. After 1.5 days at 20-25° C. the solution became a thick suspension. Using a water bath to control the exotherm, 20 mL of concentrated HCl was added. The mixture was then concentrated to remove the THF and methanol and 150 mL water was added. The solid was isolated by filtration and washed with 50 mL water. After drying under vacuum, the title compound was isolated as a white crystalline solid (9.4 g, 99% yield).

$^1$H NMR (400 MHz, DMSO-$d_6$) δ 7.95-7.89 (2H, m), 7.58 (2H, apparent td, J=7.5, 1.7 Hz), 7.48-7.41 (1H, m), 7.30-7.22 (2H, m), 7.16-7.10 (2H, m), 5.22 (2H, s).

$^{13}$C NMR (100 MHz, DMSO-$d_6$) δ 167.3, 162.1, 160.8 (d, J=246 Hz), 131.7, 131.2 (d, J=3.8 Hz), 131.0 (d, J=8.3 Hz), 124.9 (d, J=3.4 Hz), 123.8, 123.6, 115.8 (d, J=21.0 Hz), 114.9, 64.2 (d, J=3.4 Hz).

LRMS (m/e) 247.2 [MH]$^+$.

Preparation 3:
4-(2-fluorobenzyloxy)-N-methyl-N-methoxybenzamide (P3)

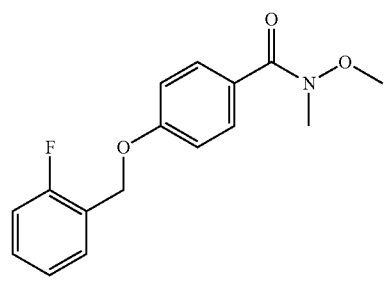 [SMILES: CON(C)C(=O)c1ccc(OCc2ccccc2F)cc1]

4-(2-fluorobenzyloxy)benzoic acid (P2, 5.5 g, 22.3 mmol) was suspended in thionyl chloride (16.5 mL) and heated to 65° C. and held for 3 hours during which time the reactor was kept under a slow sweep of nitrogen. The mixture was then concentrated to a thick oil under hi vac to remove all traces of residual thionyl chloride. The residue was then diluted in CH$_2$Cl$_2$ (20 mL) and cooled to 0° C. In a separate flask, a solution of diaza(1,3)bicycle[5.4.0]undecane (DBU, 8.0 mL, 8.15 g, 53.52 mmol) and N-methoxy-N-methyl amine hydrochloride (2.61 g, 26.76 mmol) in CH$_2$Cl$_2$ (20 mL) was made and slowly added to the solution at 0° C. After warming to 20-25° C., the mixture was washed with 1 M HCl and then with a saturated NaHCO$_3$ solution. After drying over Na$_2$SO$_4$, the solution was concentrated to a thick residue. The mixture was then purified by flash column chromatography eluting with 0→100% EtOAc/hexanes (gradient). Concentration of the fractions containing the title compound gave an oil that crystallized upon standing (6.0 g, 93% yield).

$^1$H NMR (400 MHz, DMSO-$d_6$) δ 7.66-7.62 (2H, m), 7.58 (2H, apparent td, J=7.5, 1.7 Hz), 7.48-7.41 (1H, m), 7.30-7.23 (2H, m), 7.12-7.07 (2H, m), 5.20 (2H, s), 3.55 (3H, s), 3.25 (3H, s).

$^{13}$C NMR (100 MHz, DMSO-$d_6$) δ 168.9, 168.0 (d, J=246 Hz), 163.0, 131.2 (d, J=3.8 Hz), 130.9 (d, J=8.2 Hz), 130.4, 126.9, 124.9 (d, J=3.4 Hz), 123.8 (d, J=14.8 Hz), 115.8 (d, J=21.0 Hz), 114.4, 64.0 (d, J=3.8 Hz), 60.9, 33.8.

LRMS (m/e) 290.3 [MH]$^+$.

Preparation 4: 1-(4-[2-fluorobenzyloxy]phenyl)-2-propen-1-one (P4)

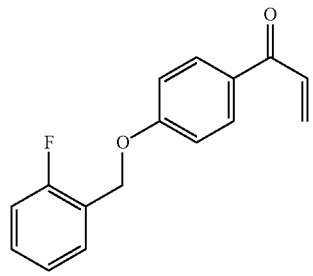 [SMILES: C=CC(=O)c1ccc(OCc2ccccc2F)cc1]

4-(2-fluorobenzyloxy)-N-methyl-N-methoxybenzamide (P3, 6.0 g, 20.7 mmol) was dissolved in THF (100 mL) and cooled to −78° C. A 1.0 M solution of vinyl magnesium bromide in THF (31 mL, 31 mmol) was added and the cold bath was removed. Upon warming to 20-25° C., the mixture was poured into a vigorously stirred solution of 1 M HCl. The resulting mixture was extracted twice with CH$_2$Cl$_2$. The combined organic layers were then washed with 1 M HCl, then with a saturated NaHCO$_3$ solution, dried over Na$_2$SO$_4$, and concentrated to a thick residue. The product was purified by flash column chromatography eluting with 0→40% acetone hexanes (gradient). Concentration of the fractions containing 4 gave an oil that crystallized upon standing (4.83 g, 91% yield).

$^1$H NMR (400 MHz, DMSO-$d_6$) δ 8.06-8.01 (2H, m), 7.59 (1H, apparent td, J=7.5, 1.7 Hz), 7.48-7.38 (2H, m), 7.30-7.22 (2H, m), 7.21-7.16 (2H, m), 6.32 (1H, dd, J=17.0, 2.0 Hz), 5.92 (1H, dd, J=10.5, 2.0 Hz), 5.26 (2H, s).

$^{13}$C NMR (100 MHz, DMSO-$d_6$) δ 188.3, 162.6, 160.8 (d, J=246 Hz), 132.5, 131.3, 131.2 (d, J=3.8 Hz), 131.0 (d, J=8.2 Hz), 130.3, 129.7, 124.9 (d, J=3.1 Hz), 123.6 (d, J=14.4 Hz), 115.8 (d, J=21.0 Hz), 115.2, 64.3 (d, J=3.4 Hz).

LRMS (m/e) 257.3 [MH]$^+$.

Preparation 5: Ethyl-5-(4-[2-fluorobenzyloxy]phenyl)-3,4-dihydro-2H-pyrrole-2-carboxyate (P5)

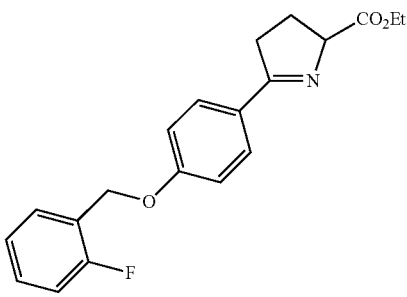 [SMILES: CCOC(=O)C1CCC(c2ccc(OCc3ccccc3F)cc2)=N1]

(S)-4-Isopropyl-2-[(S)-2-(diphenylphosphino)ferrocen-1-yl]oxazoline (18.8 mg, 0.039 mmol) and Cu(MeCN)$_4$PF$_6$ (14.5 mg, 0.039 mmol) were added to a dried, nitrogen swept reaction vessel. Anhydrous, degassed, BHT inhibited THF (5.0 mL) was then added and the mixture was stirred for 30 minutes at 20-25° C. The resulting solution was then cooled to −78° C. and a solution of 1-(4-[2-fluorobenzyloxy]phenyl)-2-propen-1-one (P4, 2.0 g, 7.80 mmol) and ethyl N-(diphenylmethylidene)glycinate (2.29 g, 8.58 mmol) in THF (15 mL total volume) was added over 1-2 minutes. After 3-5 minutes, a solution of DBU (5.9 mg, 0.039 mmol) in THF (0.5 mL total volume) was added. The solution was then stirred for 8-12 hours at −78° C. The reaction mixture was then warmed to 0-5° C. and 1 M $H_2SO_4$ (aq., 25 mL) was then added. The reaction mixture was then warmed to 20-25° C. and mixed vigorously for 2 hours. The mixture was then poured into a rapidly stirring solution of $NaHCO_3$ (saturated, enough to bring the pH to 7.0). After 5 minutes of stirring, the mixture was extracted twice with TBME and the organic extracts were pooled, dried over $Na_2SO_4$, and concentrated to near dryness. The resulting residue was purified by flash column chromatography eluting with 0→40% acetone/hexanes (gradient). Concentration of the fractions containing the title compound gave a crystalline solid (2.23 g, 84% yield).

$^1$H NMR (400 MHz, DMSO-$d_6$) δ 7.85-7.80 (2H, m), 7.58 (1H, apparent td, J=7.5, 1.7 Hz), 7.47-7.41 (1H, m), 7.30-7.22 (2H, m), 7.13-7.09 (2H, m), 5.21 (2H, s), 4.82-4.76 (1H, m), 4.14 (2H, q, J=7.1 Hz), 3.13-3.02 (1H, m), 2.98-2.87 (1H, m), 2.32-2.21 (1H, m), 2.09-1.98 (1H, m), 1.22 (3H, t, J=7.02 Hz).

$^{13}$C NMR (100 MHz, DMSO-$d_6$) δ 174.8, 173.1, 160.8 (d, J=246 Hz), 160.6, 131.1 (d, J=3.8 Hz), 130.9 (d, J=8.3 Hz), 130.0, 127.1, 124.9 (d, J=3.1 Hz), 123.9 (d, J=14.4 Hz), 115.8 (d, J=21.0 Hz), 115.0, 74.2, 64.0 (d, J=3.8 Hz), 60.7, 35.3, 26.6, 14.4.

LRMS (m/e) 342.4 [MH]$^+$.

Preparation 6: 1-{4-[(phenylmethyl)oxy]phenyl}-2-propen-1-one (P6)

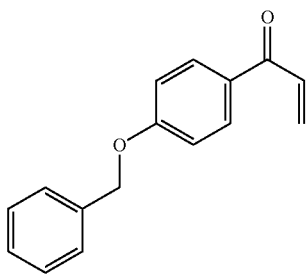 [SMILES: C=CC(=O)c1ccc(OCc2ccccc2)cc1]

1-{4-[(phenylmethyl)oxy]phenyl}-2-propen-1-one may be prepared from N-methyl-N-(methyloxy)-4-[(phenylmethyl)oxy]benzamide using analogous procedures as those described above for the preparation of P4. N-methyl-N-(methyloxy)-4-[(phenylmethyl)oxy]benzamide may be prepared according to procedures known from the literature (Cowart, M. et. al. J. Med. Chem. 2005, 48, 38).

$^1$H NMR (400 MHz, DMSO-$d_6$) δ 8.05-8.00 (2H, m), 7.50-7.32 (6H, m), 7.18-7.14 (2H, m), 6.32 (1H, dd, J=16.9, 2.1 Hz), 5.92 (1H, dd, J=10.5, 2.1 Hz), 5.23 (2H, s).

$^{13}$C NMR (100 MHz, DMSO-$d_6$) d 188.3, 162.8, 136.8, 132.5, 131.3, 130.1, 129.6, 128.9, 128.4, 128.2, 115.3, 69.9.

LRMS (m/e) 239.3 [MH]$^+$.

Preparation 7a and 7b Ethyl (2R)-2-[(diphenylmethylidene)amino]-5-(4-[benzyloxy]phenyl)-5-oxopentanoate (P7a) and Ethyl (2S)-2-[(diphenylmethylidene)amino]-5-(4-[benzyloxy]phenyl)-5-oxopentanoate (P7b)

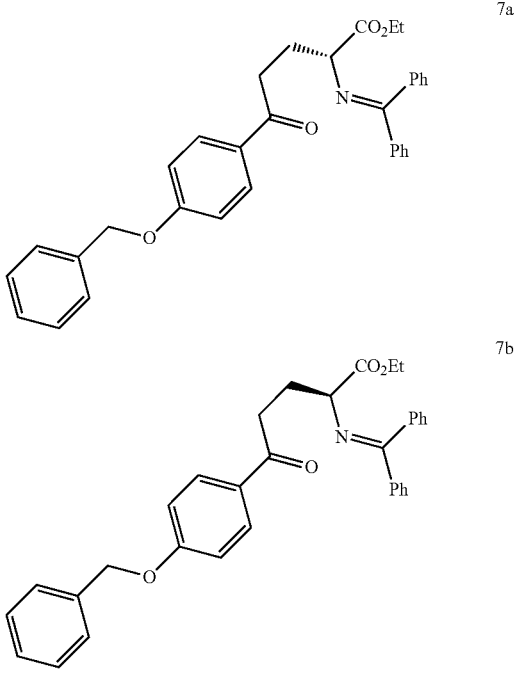

The Ligand (according to Table 1 below reported, 0.0084 mmol) and Cu(MeCN)$_4$PF$_6$ (3.13 mg, 0.0084 mmol) were added to a dried, nitrogen swept reaction vessel. Anhydrous, degassed, BHT inhibited THF (0.4 mL) was then added and the mixture was stirred for 30 minutes at 20-25° C. The resulting solution was then cooled to −20 to −21° C. and a solution of 1-{4-[(phenylmethyl)oxy]phenyl}-2-propen-1-one (P6, 100 mg, 0.42 mmol) and ethyl N-(diphenylmethylidene)glycinate (123.5 mg, 0.462 mmol) in THF (0.5 mL total volume) was added over 1-2 minutes. After 1-5 minutes, a solution of DBU (1.27 mg, 0.0084 mmol) in THF (0.1 mL total volume) was added. The solution was then stirred for 8-12 hours at −20 to −25° C. After this time the reactions were complete and an aliquot of each reaction mixture was diluted in 10% iPrOH/hexanes and analyzed by chiral HPLC. An analytically pure sample was obtained by subjecting the concentrated reaction mixture to flash column chromatography eluting with 0→40% acetone hexanes (gradient). Concentration of the fractions containing 7a and 7b (94:6) gave a thick syrup (187 mg, 88% yield).

$^1$H NMR (400 MHz, DMSO-$d_6$) δ 7.91-7.86 (2H, m), 7.54-7.32 (13H, m), 7.13-7.07 (4H, m), 5.20 (2H, s), 4.11-4.05 (2H, m), 4.02 (1H, dd, J=8.0, 4.8 Hz), 3.01-2.91 (2H, m), 2.27-2.21 (1H, m), 2.14-2.08 (1H, m), 1.16 (3H, t, J=7.2 Hz).

$^{13}$C NMR (100 MHz, DMSO-$d_6$) δ 197.3, 171.2, 170.0, 162.1, 138.8, 136.5, 135.6, 130.5, 130.1, 129.6, 128.7, 128.6, 128.5, 128.2, 128.1, 128.0, 127.7, 127.3, 114.6, 69.4, 63.8, 60.5, 33.6, 27.7, 14.0.

Corresponding to the ligand used, the ratio of P7a to P7b obtained based on peak area is reported below in table 1.

TABLE 1

| Ligand Family | R1 | R2 | P7a | P7b |
|---|---|---|---|---|
| Josiphos (R)-1-[(S)-2-(Diphenylphosphino)ferrocenyl]ethyldicyclohexylphosphine ethanol adduct | Ph | Cy | 1 | 99 |
| Josiphos (R)-1-[(S)-2-Diphenylphosphinoferrocenyl]ethyldi-tert.-butylphosphine | Ph | t-But | 7 | 93 |
| Josiphos (R)-1-[(S)-2-Dicyclohexylphosphino)ferrocenyl]ethyldicyclohexylphosphine | Cy | Cy | 68 | 32 |
| Josiphos (R)-1-[(S)-2-Diphenylphosphino)-ferrocenyl]ethyl-di-3,5-xylylphosphine | Ph | 3,5-dimethylphenyl | 8 | 92 |
| Josiphos (R)-1-[(S)-2-Di-(3,5-bis(trifluoromethyl)phenyl)phosphino)-ferrocenyl]ethyldicyclohexylphosphine | 3,5-di-(trifluoromethyl)phenyl | Cy | 2.5 | 97.5 |
| Josiphos (R)-1-[(S)-2-Di-(4-methoxy-3,5-dimethylphenyl)phosphino)-ferrocenyl]ethyldicyclohexylphosphine | 3,5-dimethyl-4-methoxyphenyl | Cy | 4 | 96 |
| Josiphos (R)-1-[(S)-2-Di-(3,5-bis(trifluoromethyl)phenyl)phosphino)-ferrocenyl]ethyldi-(3,5-xylyl)phosphine | 3,5-di-(trifluoromethyl)phenyl | 3,5-dimethylphenyl | 4 | 96 |
| Josiphos (R)-1-[(S)-2-Dicyclohexylphosphino)ferrocenyl]-ethyldi-tert.-butylphosphine | Cy | t-But | 23 | 77 |
| Josiphos (R)-1-[(S)-2-Di-(4-trifluoromethylphenyl)phosphino)ferrocenyl]ethyldi-tert.-butylphosphine | 4-trifluorophenyl-methyl | t-But | 6 | 94 |
| Josiphos (R)-1-[(S)-2-(Di-2-furylphosphino)-ferrocenyl]ethyldi-3,5-xylylphosphine | 2-furanyl | 3,5-dimethylphenyl | 58 | 42 |

TABLE 1-continued

| Ligand Family | R1 | R2 | P7a | P7b |
|---|---|---|---|---|
| Naud<br><br>(R)-4-Isopropyl-2-[(R)-2-<br>(diphenylphosphino)<br>ferrocen-1-yl]oxazoline | | Ph | i-Pr | 94 | 6 |
| Taniaphos<br><br>(S)-1-Diphenylphosphino-2-<br>[(R)-□-<br>(N,N-dimethylamino)-o-<br>diphenylphosphinophenyl)<br>methyl]ferrocene | | | 62 | 38 |
| Walphos<br><br>(R)-1-[(R)-2-(2i-<br>Diphenylphosphinophenyl)<br>ferrocenyl]ethyldi(bis-<br>3,5-trifluoromethylphenyl)<br>phosphine | Ph | 3,5-di-<br>(trifluoromethyl)<br>phenyl | 33 | 67 |
| Walphos<br>(R)-1-[(R)-2-(2i-<br>Diphenylphosphinophenyl)<br>ferrocenyl]-<br>ethyldiphenylphosphine | Ph | Ph | 41 | 59 |

TABLE 1-continued

| Ligand Family | R1 | R2 | P7a | P7b |
|---|---|---|---|---|
| Walphos<br><br>(S)-1-[(S)-2-{2i-Di(3,5-dimethyl-4-methoxyphenyl)phosphino-phenyl}-ferrocenyl]ethyldi(bis-3,5-trifluoromethylphenyl) phosphine | 3,5-dimethyl-4-methoxyphenyl | 3,5-di-(trifluoromethyl) phenyl | 47 | 53 |
| Mandyphos<br><br>(αR, αR)-2,2i-Bis(α-N,N-dimethylaminophenylmethyl)-(S,S)-1,1 ibis(diphenylphosphino) ferrocene | R = Ph | | 15 | 85 |
| Mandyphos (αR, αR)-2,2i-Bis(α-N,N-dimethylaminophenylmethyl)-(S,S)-1,1 ibis (dicyclohexylphosphino)-ferrocene | R = Cy | | 60 | 40 |
| Mandyphos (αR, αR)-2,2i-Bis(α-N,N-dimethylaminophenyl methyl)-(S,S)-1,1 i-bis-[di(bis-3,5-trifluoromethyl)phenyl)-phosphino]ferrocene | R = 3,5-di-(trifluoromethyl) phenyl | | 74 | 26 |
| Mandyphos (αR, αR)-2,2i-Bis(α-N,N-dimethylaminophenyl methyl)-(S,S)-1,1 ibis[di(3,5-dimethyl-4-methoxyphenyl)phosphino]ferrocene | R = 3,5-dimethyl-4-methoxyphenyl | | 18 | 82 |
| Hydroquinidine(anthraquinone-1,4-diyl) diether | | | 54 | 46 |

TABLE 1-continued

| Ligand Family | R1 | R2 | P7a | P7b |
|---|---|---|---|---|
| 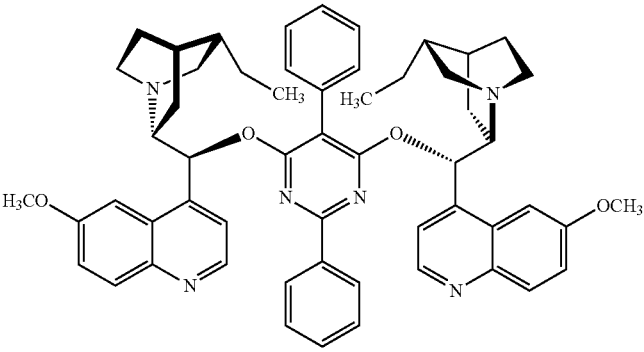 Hydroquinidine-2,5-diphenyl-4,6-pyrimidinediyl diether | | | 61 | 39 |
| 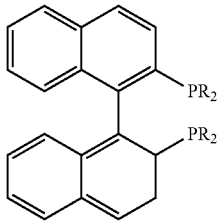 (R)-(+)-2,2'-Bis(di-p-tolylphosphino)-1,1'-binaphthyl | R = p-tolyl | | 89 | 11 |

EXAMPLE 1

(5R)-5-(4-[2-fluorobenzyloxy]phenyl)-L-prolinamide (E1)

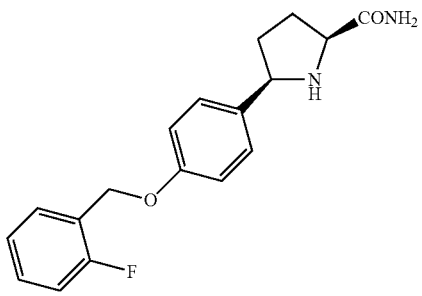 [SMILES: NC(=O)[C@@H]1CC[C@H](c2ccc(OCc3ccccc3F)cc2)N1]

A mixture of 5% Pt/C (Johnson Mathey B102022-5, 100 mg) was added to a solution of Ethyl-5-(4-[2-fluorobenzyloxy]phenyl)-3,4-dihydro-2H-pyrrole-2-carboxylate (P5, obtained as above reported, 1.0 g, 2.93 mmol) in ethanol (12 mL). Acetic acid (1.2 mL) was then added and the reaction vessel was purged with $N_2$ and then $H_2$. The mixture was hydrogenated at 50 psi of $H_2$ at 15-20° C. for at least 2 h. Upon completion of the reaction (monitored by $H_2$ uptake), the mixture was filtered through celite, then through a 0.2 μm PTFE filter and concentrated to approximately 1.5 mL. The mixture was diluted with 1:1 iPrOAc/TBME and washed with a saturated solution of $NaHCO_3$. After concentrating the organics to a thick residual oil (986 mg, 98% crude yield; LCMS retention time 2.04 minutes, calculated 344.4 [MH]$^+$, found 344.3 [MH]$^+$), a solution of ammonia in methanol (ca 7 M) was added in two portions (4 mL initially and then 1 mL after ~10 hrs). After the additions were complete, the reaction stirred for at least 24 hrs at 15-20° C. Upon completion of the reaction, the mixture was concentrated to dryness. The solid was suspended in a mixture of toluene/TBME 1:1 (~4 mL) at 18-23° C. with vigorous mixing. After 2 hrs at 18-23° C., the mixture was cooled to 0-5° C. and held for 1 hr. The solid was isolated by filtration and washed with TBME (~4 mL). Drying the solid in a vacuum oven at approximately 40° C. gave the title compound as an off white-solid (720 mg, 78% yield from P5).

Analysis of the sample obtained, performed on CHIRAL-CEL OJ analytical HPLC column (10% iPrOH/hexanes, 1 mL/min, rt), revealed the presence in minor amounts of (5S)-5-(4-{[(2-fluorophenyl)methyl]oxy}phenyl)-D-prolinamide (enantiomer of the title compound); retention times: (5S)-5-(4-{[(2-fluorophenyl)methyl]oxy}phenyl)-D-prolinamide 36.3 min (1.2%), E1 41.8 min (98.8%).

$^1$H NMR (400 MHz, DMSO-d$_6$) δ 7.55 (1H, apparent td, J=7.6, 1.6 Hz), 7.45-7.32 (4H, m), 7.29-7.21 (2H, m), 7.14 (1H, br. s), 7.00-6.95 (2H, m), 5.12 (2H, s), 4.10 (1H, dd, J=9.4, 5.8 Hz), 3.56 (1H, dd, J=9.4, 4.4 Hz), 2.14-1.96 (2H, m), 1.92-1.82 (1H, m), 1.47-1.36 (1H, m).

$^{13}$C NMR (100 MHz, DMSO-d$_6$) δ 177.1, 160.3 (d, J=246 Hz), 157.0, 137.1, 130.6 (d, J=3.8 Hz), 130.3 (d, J=8.3 Hz), 127.6, 124.5 (d, J=3.4 Hz), 124.0 (d, J=14.4 Hz), 115.3 (d, J=21.0 Hz), 114.4, 63.5 (d, J=3.8 Hz), 61.7, 59.9, 34.1, 30.4.

EXAMPLE 2

(5R)-5-(4-[2-fluorobenzyloxy]phenyl)-L-prolinamide hydrochloride (E2)

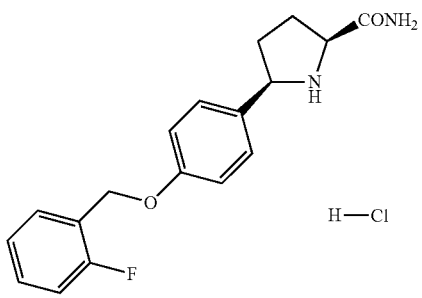 [SMILES: NC(=O)[C@@H]1CC[C@H](c2ccc(OCc3ccccc3F)cc2)N1 ; Cl]

To a solution of E1 (72 mg, 0.23 mmol) in a mixture of ethyl acetate (1.0 ml) and methanol (1.0 ml) was added 4M HCl in 1,4-dioxane (57.5 uL, 0.23 mmol) at 0° C. The mixture was stirred for 1.5 h and slowly allowed to warm to room temperature. After evaporating the solvent, the residue was triturated with diethyl ether to afford the title compound as a white solid (75 mg, 93% yield).

$^1$H NMR (300 MHz, DMSO-$d_6$) δ 10.89 (1H, br. s), 8.12 (1H, s), 8.11 (1H, br. s), 7.73 (1H, s), 7.60-7.39 (4H, m), 7.30-7.21 (2H, m), 7.13-7.06 (2H, m), 5.18 (2H, s), 4.66-4.56 (1H, m), 4.36-4.28 (1H, m), 2.42-1.94 (4H, m).

The invention claimed is:

1. A process for the preparation of (5R)-5-(4-{[(2-fluorophenyl)methyl]oxy}phenyl)-L-prolinamide represented by Formula (A)

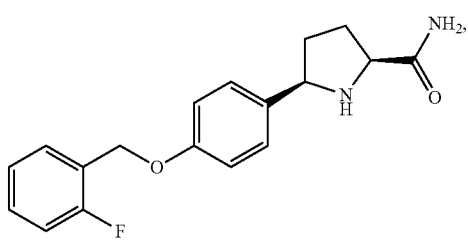

which comprises:

(a) reacting 1-(4-[2-fluorobenzyloxy]phenyl)-2-propen-1-one which is represented by Formula (B)

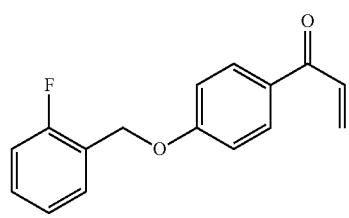

with a compound of Formula (III)

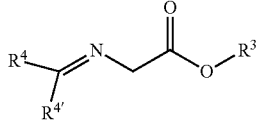

wherein $R^3$ is $C_{1-4}$ alkyl and $R^4$ and $R^{4'}$ are each independently an optionally substituted phenyl in the presence of reagents consisting essentially of an organic aprotic solvent, an amine base, a chiral ligand and an appropriate Cu(I) salt, under conditions of time and temperature sufficient to produce the corresponding intermediate represented by Formula (C)

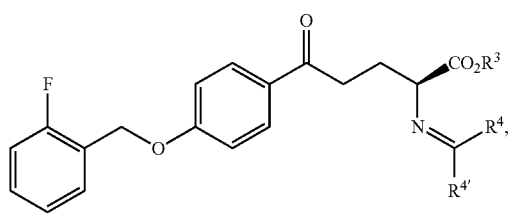

wherein the chiral ligand is selected in the group consisting of:
(R)-1-[(S)-2-(Diphenylphosphino)ferrocenyl]ethyldicyclohexylphosphine ethanol adduct;
(S)-1-[(R)-2-(Diphenylphosphino)ferrocenyl]ethyldicyclohexylphosphine ethanol adduct;
(R)-1-[(S)-2-Diphenylphosphinoferrocenyl]ethyldi-tert-butylphosphine;
(S)-1-[(R)-2-Diphenylphosphinoferrocenyl]ethyldi-tert-butylphosphine;
(R)-1-[(S)-2-Dicyclohexylphosphino)ferrocenyl]ethyldicyclohexylphosphine;
(S)-1-[(R)-2-Dicyclohexylphosphino)ferrocenyl]ethyldicyclohexylphosphine;
(R)-1-[(S)-2-Diphenylphosphino)-ferrocenyl]ethyl-di-3,5-xylylphosphine;
(S)-1-[(R)-2-Diphenylphosphino)-ferrocenyl]ethyl-di-3,5-xylylphosphine;
(R)-1-[(S)-2-Di-(3,5-bis(trifluoromethyl)phenyl)phosphino)-ferrocenyl]ethyldicyclohexylphosphine;
(S)-1-[(R)-2-Di-(3,5-bis(trifluoromethyl)phenyl)phosphino)-ferrocenyl]ethyldicyclohexylphosphine;
(R)-1-[(S)-2-Di-(4-methoxy-3,5-dimethylphenyl)phosphino)-ferrocenyl]ethyldicyclohexylphosphine;
(S)-1-[(R)-2-Di-(4-methoxy-3,5-dimethylphenyl)phosphino)-ferrocenyl]ethyldicyclohexylphosphine;
(R)-1-[(S)-2-Di-(3,5-bis(trifluoromethyl)phenyl)phosphino)-ferrocenyl]ethyldi-(3,5-xylyl)phosphine;
(S)-1-[(R)-2-Di-(3,5-bis(trifluoromethyl)phenyl)phosphino)-ferrocenyl]ethyldi-(3,5-xylyl)phosphine;
(R)-1-[(S)-2-Dicyclohexylphosphino)ferrocenyl]-ethyldi-tert-butylphosphine;
(S)-1-[(R)-2-Dicyclohexylphosphino)ferrocenyl]-ethyldi-tert-butylphosphine;
(R)-1-[(S)-2-Di-(4-trifluoromethylphenyl)phosphino)ferrocenyl]ethyldi-tert-butylphosphine;
(S)-1-[(R)-2-Di-(4-trifluoromethylphenyl)phosphino)ferrocenyl]ethyldi-tert-butylphosphine;

(R)-1-[(S)-2-(Di-2-furylphosphino)-ferrocenyl]ethyldi-3,5-xylylphosphine;
(S)-1-[(R)-2-(Di-2-furylphosphino)-ferrocenyl]ethyldi-3,5-xylylphosphine;
(R)-4-Isopropyl-2-[(R)-2-(diphenylphosphino)ferrocen-1-yl]oxazoline;
(S)-4-Isopropyl-2-[(S)-2-(diphenylphosphino)ferrocen-1-yl]oxazoline;
(S)-1-Diphenylphosphino-2-[(R)-[alpha]-(N,N-dimethylamino)-o-diphenylphosphinophenyl)methyl]ferrocene;
(R)-1-Diphenylphosphino-2-[(S)-[alpha]-(N,N-dimethylamino)-o-diphenylphosphinophenyl)methyl]ferrocene;
(R)-1-[(R)-2-(2'-Diphenylphosphinophenyl)ferrocenyl]ethyldi(bis-3,5-trifluoromethylphenyl)phosphine;
(S)-1-[(S)-2-(2'-Diphenylphosphinophenyl)ferrocenyl]ethyldi(bis-3,5-trifluoromethylphenyl)phosphine;
(R)-1-[(R)-2-(2'-Diphenylphosphinophenyl)ferrocenyl]-ethyldiphenylphosphine;
(S)-1-[(S)-2-(2'-Diphenylphosphinophenyl)ferrocenyl]ethyldiphenylphosphine;
(S)-1-[(S)-2-{2'-Di(3,5-dimethyl-4-methoxyphenyl)phosphinophenyl}-ferrocenyl]ethyldi(bis-3,5-trifluoromethylphenyl)phosphine;
(R)-1-[(R)-2-{2'-Di(3,5-dimethyl-4-methoxyphenyl)phosphinophenyl}-ferrocenyl]ethyldi(bis-3,5-trifluoromethylphenyl)phosphine;
([alpha]R,[alpha]R)-2,2'-Bis([alpha]-N,N-dimethylaminophenylmethyl)-(S,S)-1,1'-bis(diphenylphosphino)ferrocene;
([alpha]S,[alpha]S)-2,2'-Bis([alpha]-N,N-dimethylaminophenylmethyl)-(R,R)-1,1'-bis(diphenylphosphino)ferrocene;
([alpha]R,[alpha]R)-2,2'-Bis([alpha]-N,N-dimethylaminophenylmethyl)-(S,S)-1,1'-bis(dicyclohexyl phosphino)-ferrocene;
([alpha]S,[alpha]S)-2,2'-Bis([alpha]-N,N-dimethylaminophenylmethyl)-(R,R)-1,1'-bis(dicyclohexylphosphino)-ferrocene;
([alpha]R,[alpha]R)-2,2'-Bis([alpha]-N,N-dimethylaminophenylmethyl)-(S,S)-1,1'-bis-Ni(bis-(3,5-trifluoromethyl)phenyl)-phosphino]ferrocene;
([alpha]S,[alpha]S)-2,2'-Bis([alpha]-N,N-dimethylaminophenylmethyl)-(R,R)-1,1'-bis-[di(bis-(3,5-trifluoromethyl)phenyl)-phosphino]ferrocene;
([alpha]R,[alpha]R)-2,2'-Bis([alpha]-N,N-dimethylaminophenylmethyl)-(S,S)-1,1'-bis[di(3,5-dimethyl-4-methoxyphenyl)phosphino]ferrocene;
([alpha]S,[alpha]S)-2,2'-Bis([alpha]-N,N-dimethylaminophenylmethyl)-(R,R)-1,1'-bis[di(3,5-dimethyl-4-methoxyphenyl)phosphino]ferrocene;
Hydroquinidine(anthraquinone-1,4-diyl)diether;
Hydroquinidine-2,5-diphenyl-4,6-pyrimidinediyl diether;
(S)-(−)-2,2'-Bis(di-p-tolylphosphino)-1,1'-binaphthyl and (R)-(+)-2,2'-Bis(di-p-tolylphosphino)-1,1'-binaphthyl;

(b) reacting a compound of Formula (C) in aqueous acidic media under conditions of time and temperature sufficient to produce the compound of Formula (D) after neutralization with an appropriate base

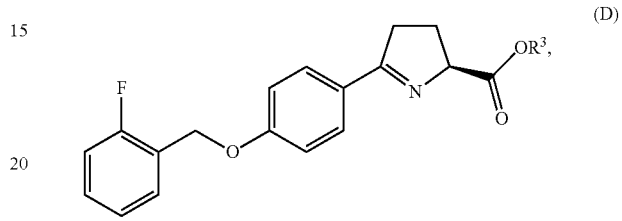

(c) reacting a compound of Formula (D) with Pt/C under an atmosphere of hydrogen at elevated pressure in a suitable protic solvent at room temperature for a time sufficient to give a compound of formula (E)

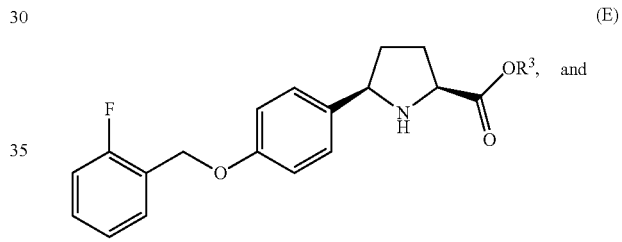

(d) reacting a compound of Formula (E) with a solution of NH₃ in an appropriate protic solvent and at the appropriate temperature for a period of time sufficient to produce (5R)-5-(4-{[(2-fluorophenyl)methyl]oxy}phenyl)-L-prolinamide.

2. A process according to claim 1, wherein for step (a) the ligand is (s)-4-Isopropyl-2-[(S)-2-(diphenylphosphino)ferrocen-1-yl]oxazoline and the Cu(I) complex is Cu(MeCN)$_4$PF$_6$.

* * * * *

UNITED STATES PATENT AND TRADEMARK OFFICE
CERTIFICATE OF CORRECTION

| | | |
|---|---|---|
| PATENT NO. | : 8,759,542 B2 | Page 1 of 1 |
| APPLICATION NO. | : 13/393174 | |
| DATED | : June 24, 2014 | |
| INVENTOR(S) | : Matthew Allen Zajac | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 39 days.

Signed and Sealed this
Eighth Day of September, 2015

Michelle K. Lee
*Director of the United States Patent and Trademark Office*